United States Patent
Daub et al.

(10) Patent No.: US 12,346,877 B2
(45) Date of Patent: Jul. 1, 2025

(54) DATABASE MANAGEMENT SYSTEM UTILIZING A MOBILE ELECTRONIC DEVICE

(71) Applicant: STCHealth, LLC, Phoenix, AZ (US)

(72) Inventors: Erich Daub, Stone Mountain, GA (US); David A. Rose, Huntingdon Valley, PA (US); Robert Perry, Tucson, AZ (US); Todd Watkins, Albuquerque, NM (US); Michael L. Popovich, Tucson, AZ (US); Judy Merritt, Norman, OK (US); Pamela L. Schwartz, Harrisburg, NC (US); Joe Kelly, Phoenix, AZ (US); Kristina Crane, Phoenix, AZ (US)

(73) Assignee: STCHealth, LLC, Phoenix, AZ (US)

( * ) Notice: Subject to any disclaimer, the term of this patent is extended or adjusted under 35 U.S.C. 154(b) by 1145 days.

(21) Appl. No.: 17/170,581

(22) Filed: Feb. 8, 2021

(65) Prior Publication Data
US 2021/0158292 A1    May 27, 2021

Related U.S. Application Data

(63) Continuation-in-part of application No. 15/913,107, filed on Mar. 6, 2018, now Pat. No. 10,915,864, which is a continuation of application No. 14/036,476, filed on Sep. 25, 2013, now abandoned.

(51) Int. Cl.
G06Q 50/00    (2024.01)
G06Q 10/10    (2023.01)
G16H 10/60    (2018.01)
G16H 80/00    (2018.01)
H04W 4/60    (2018.01)

(52) U.S. Cl.
CPC ............ *G06Q 10/10* (2013.01); *G16H 10/60* (2018.01); *G16H 80/00* (2018.01); *H04W 4/60* (2018.02)

(58) Field of Classification Search
CPC ........ G06Q 10/10; G16H 10/60; G16H 80/00; G16H 10/40; G16H 10/65; G16H 15/00; G16H 40/20; G16H 40/06; H04W 4/60; H04L 63/08
See application file for complete search history.

(56) References Cited

U.S. PATENT DOCUMENTS

| | | | |
|---|---|---|---|
| 8,117,045 B2 | 2/2012 | Lorsch | |
| 8,117,646 B2 | 2/2012 | Lorsch | |
| 8,121,855 B2 | 2/2012 | Lorsch | |
| 8,301,466 B2 | 10/2012 | Lorsch | |
| 8,498,883 B2 | 7/2013 | Lorsch | |
| 11,587,688 B2* | 2/2023 | Joao | H04L 12/1818 |
| 2009/0319296 A1* | 12/2009 | Schoenberg | G16H 10/60 705/2 |
| 2010/0256994 A1* | 10/2010 | Eisenberger | G16H 40/67 726/30 |

(Continued)

*Primary Examiner* — Maroun P Kanaan
(74) *Attorney, Agent, or Firm* — SNELL & WILMER L.L.P.

(57) ABSTRACT

A private networked database system utilizing mobile devices offers centralized access, reconciliation, and sharing of data, for example consumer immunization information. The system provides technical features not previously available, including bidirectional data transmission and replication across government-controlled databases located in multiple states.

21 Claims, 14 Drawing Sheets

(56) References Cited

U.S. PATENT DOCUMENTS

| | | | |
|---|---|---|---|
| 2011/0202556 A1* | 8/2011 | Fernandez | G16H 10/60 707/769 |
| 2012/0078664 A1* | 3/2012 | Hasan | G16H 10/60 705/3 |
| 2013/0054271 A1* | 2/2013 | Langford | G16H 10/60 705/3 |
| 2014/0006038 A1* | 1/2014 | Harris | G06Q 10/10 705/2 |

* cited by examiner

Patient Vaccination and Forecast Record

Facility: STATE PRIVATE PROVIDER
Date: August 6, 2012

Patient ID: 81
Name: CHRISTINA CARLIN
Birth Date: 12/21/2003
Sex:
Guardian: AMY CARLIN Medicaid No:

Phone:
Street: 2671 AUSTIN SECRET LANE
City: CHALMETTE
State: LA
Zip: 70043

WIC ID:

Vaccination Summary

| Vaccine Name | Dose 1 | Dose 2 | Dose 3 | Dose 4 |
|---|---|---|---|---|
| DTaP/DTP/Td | 02/21/2004 | 04/24/2004 | 06/30/2004 | 12/21/2004 |
| OPV/IPV | 02/21/2004 | 04/24/2004 | 06/30/2004 | |
| MMR | 12/21/2004 | 12/21/2007 | | |
| Hep B - 3 Dose | 12/21/2003 | 05/21/2004 | 07/21/2004 | |
| Varicella | 12/21/2004 | 12/15/2009 | 12/10/2010 | 12/10/2011 |
| Influenza | 10/15/2009 | | | |

Forecast

| Vaccine Family | Dose | Scheduled Date | Minimum Valid Date |
|---|---|---|---|
| POLIO | 4 | 12/21/2007 | 12/21/2007 |
| VARICELLA | 2 | 01/18/2008 | 01/18/2008 |
| Tdap | 1 | 12/21/2010 | 12/21/2010 |
| FLU | 5 | 10/01/2012 | 10/01/2012 |
| MENINGOCOCCAL | 1 | 12/21/2014 | 12/21/2014 |

FIG. 2F

DATABASE MANAGEMENT SYSTEM UTILIZING A MOBILE ELECTRONIC DEVICE

CROSS-REFERENCE TO RELATED APPLICATIONS

This application is a continuation-in-part of U.S. Ser. No. 15/913,107 filed on Mar. 6, 2018, entitled "DATABASE MANAGEMENT SYSTEM UTILIZING A MOBILE ELECTRONIC DEVICE", which is a continuation of U.S. Ser. No. 14/036,476 filed on Sep. 25, 2013, entitled "HEALTH RECORDS MANAGEMENT SYSTEMS AND METHODS" (now Abandoned). The entire contents of the foregoing applications are incorporated by reference herein for all purposes.

TECHNICAL FIELD

The present disclosure generally relates to database management, and more particularly, to systems that reconcile and integrate information from multiple separated databases, for example government-controlled databases located in different states.

BACKGROUND

Current health records technologies suffer from gaps in the healthcare software space. For example, in general, immunization records for a particular individual may be fragmented among various entities, databases, and so forth. Accordingly, it may be difficult and/or impossible to determine a comprehensive immunization status for a particular individual. Moreover, patient access to their own immunization records can be complex, time-consuming, and/or expensive. Yet further, a parent may be unable to view immunization information for his or her child in a common system.

Immunization levels in the United States are below targeted levels desirable to minimize the incidence of vaccine preventable disease. Additionally, immunization programs typically result in cost savings of 500% or more in direct medical costs as compared to immunization expenses. Accordingly, improved systems and methods for accessing, grouping, utilizing, reporting, and/or otherwise managing health records, for example immunization records, are desirable.

SUMMARY

In an embodiment, a networked database system includes a software application for operation on a mobile electronic device. The system comprises a mobile device processor configured for manipulation of user immunization records, a tangible, non-transitory electronic memory in electronic communication with the processor, and a micro-application operative on the mobile device, the micro-application comprising an electronic database resident in the memory and a consumer software module accessible by a user of the mobile electronic device.

The micro-application is operative to: receive, from the user and via an input component of the mobile electronic device, an authorization request for the user to access the networked database system; transmit, over a network connection of the mobile electronic device and to a computer associated with a health care provider, a request for the health care provider to approve access of the user to the networked database system; receive, over the network connection of the mobile electronic device and from the computer associated with the health care provider, approval for access of the user to the networked database system; transmit, over the network connection of the mobile electronic device and to an electronic immunization registry system of a first state, a Health Level 7 (HL7) formatted request for the first state's electronic immunization records of the user; receive, over the network connection of the mobile electronic device and from the electronic immunization registry system of the first state, the first state immunization records of the user in an HL7 compatible format; transmit, over the network connection of the mobile electronic device and to an electronic immunization registry system of a second state, a Health Level 7 (HL7) formatted request for the second state's electronic immunization records of the user; receive, over the network connection of the mobile electronic device and from the electronic immunization registry system of the second state, the second state immunization records of the consumer in an HL7 compatible format; integrate, in the electronic database of the micro-application, the first state immunization records of the user and the second state immunization records of the user to form an integrated electronic immunization record of the user; transmit, over the network connection of the mobile electronic device and to the electronic immunization registry system of the first state, immunization information of the user that is present in the integrated electronic immunization record but not present in the electronic immunization registry system of the first state; transmit, over the network connection of the mobile electronic device and to the electronic immunization registry system of the second state, immunization information of the consumer that is present in the integrated electronic immunization record but not present in the electronic immunization registry system of the second state; and display, on a display of the mobile device, the integrated electronic immunization record for the user.

The contents of this summary section are provided only as a simplified introduction to the disclosure, and are not intended to be used to limit the scope of the appended claims.

BRIEF DESCRIPTION OF THE DRAWINGS

With reference to the following description, appended claims, and accompanying drawings:

FIG. 2F illustrates an exemplary immunization and forecasting report of an exemplary consumer health record access system in accordance with various embodiments;

DETAILED DESCRIPTION

Figure 1:
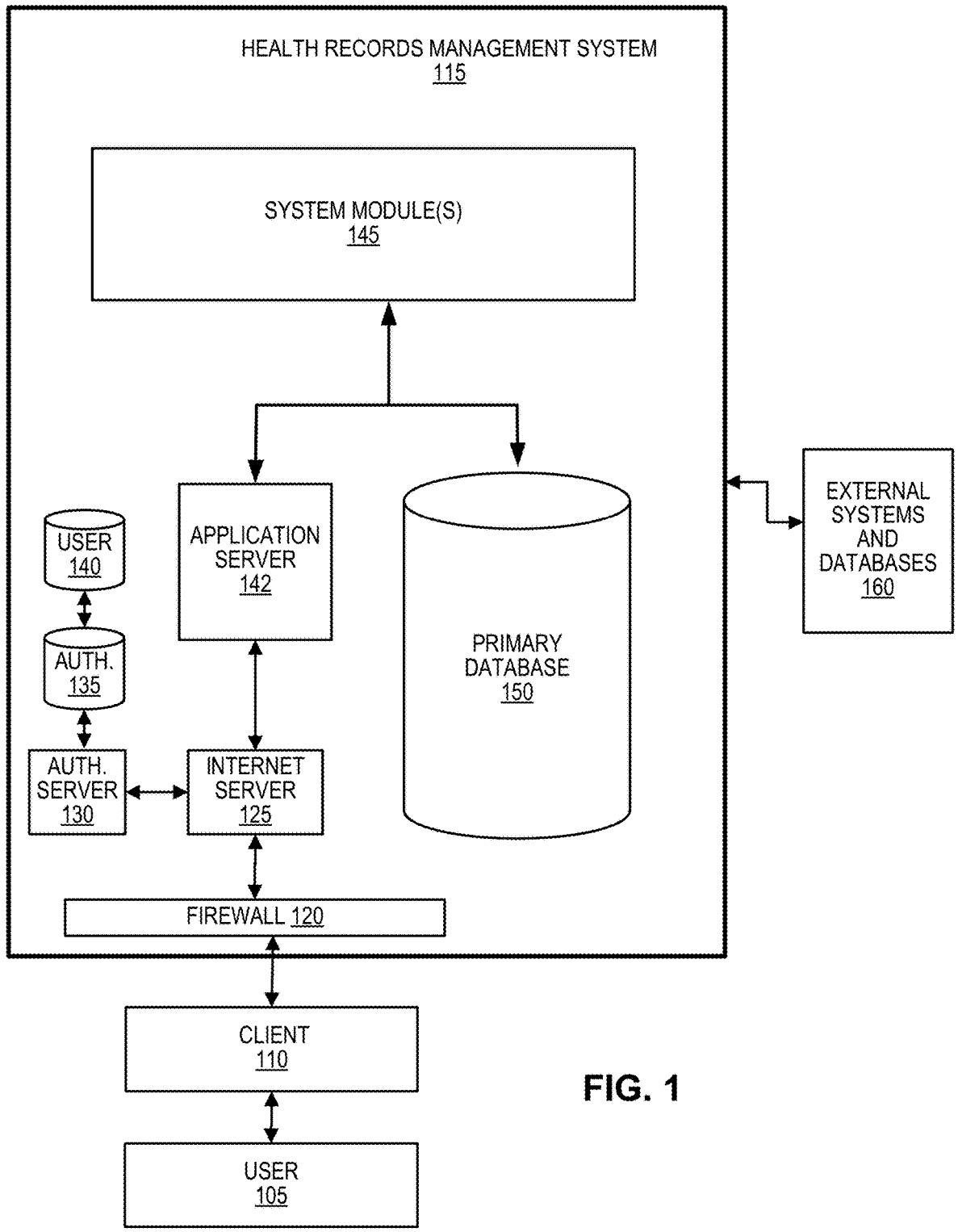
FIG. 1 is a block diagram illustrating exemplary health records management system components, in accordance with various embodiments.

The following description is of various embodiments only, and is not intended to limit the scope, applicability or configuration of the present disclosure in any way. Rather, the following description is intended to provide a convenient illustration for implementing various embodiments including the best mode. As will become apparent, various changes may be made in the function and arrangement of the elements described in these embodiments without departing from the scope of the present disclosure or appended claims.

It should be appreciated that exemplary components and steps may be realized by any number of hardware, software, or other components configured to perform the specified functions. For example, an exemplary embodiment employs various graphical user interfaces, software components, and networking and/or database functionality. In addition, various embodiments may be practiced in any number of medical record management and/or information management contexts, and the embodiments disclosed are merely indicative of exemplary applications. For example, the principles, features and methods discussed may be applied to various industries, and are not limited to use in connection with health records and/or immunizations.

The detailed description of exemplary embodiments herein makes reference to the accompanying drawings and pictures, which show various embodiments by way of illustration. While these various embodiments are described in sufficient detail to enable those skilled in the art to practice the disclosure, it should be understood that other embodiments may be realized and that logical and/or functional changes may be made without departing from the spirit and scope of the disclosure. Thus, the detailed description herein is presented for purposes of illustration only and not of limitation. For example, the steps recited in any of the method or process descriptions may be executed in various orders and are not limited to the order presented. Moreover, certain of the functions or steps may be outsourced to or performed by one or more third parties. Furthermore, any reference to singular includes plural embodiments, and any reference to more than one component may include a singular embodiment.

Systems, methods and computer program products are provided. In the detailed description herein, references to "an exemplary embodiment", "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

As used herein, "match" or "associated with" or similar phrases may include an identical match, a partial match, meeting certain criteria, matching a subset of data, a correlation, satisfying certain criteria, a correspondence, an association, an algorithmic relationship and/or the like. Similarly, as used herein, "authenticate" or similar terms may include an exact authentication, a partial authentication, authenticating a subset of data, a correspondence, satisfying certain criteria, an association, an algorithmic relationship and/or the like.

In various embodiments, the methods described herein are implemented using the various particular machines described herein. The methods described herein may be implemented using the below particular machines, and those hereinafter developed, in any suitable combination, as would be appreciated immediately by one skilled in the art. Further, as is unambiguous from this disclosure, the methods described herein may result in various transformations of certain articles.

For the sake of brevity, conventional techniques for data networking, software application development, cloud computing, and/or the like, may not be described in detail herein. Furthermore, the connecting lines shown in various figures contained herein are intended to represent exemplary functional relationships and/or physical or communicative couplings between various elements. It should be noted that many alternative or additional functional relationships or physical or communicative connections may be present in a practical health records management system.

A health records management system may be any system configured to facilitate storage and/or transmission of health records information, for example information regarding immunizations. With reference now to FIG. 1, in various exemplary embodiments a health records management system, for example system 115, is configured to provide vaccine administration records functionality, reminders, vaccination reports, vaccine inventory levels, demand forecasts, and the like.

In general, system 115 may comprise any systems, components, and/or modules (e.g., system modules 145) configured with any suitable methods, algorithms, and/or techniques for health records management. Additionally, system 115 may also suitably interface with any number and/or type of external systems 160, for example client computers, medical provider computers, government computers and the like, for example via a common network such as the Internet.

Principles of the present disclosure contemplate improved health records management methods and systems. By providing a centralized repository for health records, system users can achieve faster and simpler access to immunization information, immunization reminders, family member evaluations, and so forth. Moreover, systems and methods configured in accordance with principles of the present disclosure result in improved public health outcomes, for example increased immunization levels.

In various exemplary embodiments, according to principles of the present disclosure, systems and methods are configured to provide conditioned access to public health records, for example immunization records. As opposed to conventional medical records systems that leverage the electronic medical records of a clinical healthcare provider, systems and methods of the present disclosure leverage a central population public health data system (for example, one or more state immunization registries).

In various embodiments, exemplary health records management systems include a user interface ("UI"), software modules, logic engines, various databases, interfaces to systems and tools, and/or computer networks. While exemplary health records management systems may contemplate upgrades or reconfigurations of existing processes and/or systems, changes to existing databases and system tools are not necessarily required by principles of the present disclosure.

As used herein, an "entity" may include any individual, software program, business, organization, government entity, web site, system, hardware, and/or any other entity. A "user" may include any entity that interacts with a system and/or participates in a process. In various exemplary embodiments, a user is one or more of a consumer, a healthcare provider, or a representative of a state immunization registry.

Continuing to reference FIG. 1, in accordance with various embodiments, a user 105 may perform tasks such as requesting, retrieving, receiving, updating, analyzing and/or modifying data. User 105 may also perform tasks such as initiating, manipulating, interacting with or using a software application, tool, module or hardware, and initiating, receiving or sending a communication. User 105 may interface with Internet server 125 via any communication protocol, user device or method discussed herein, known in the art, or later developed. User 105 may be, for example, a patient, a medical provider, a state records administrator, a health records provider, and/or the like. In various embodiments, a user device may comprise software and/or hardware in communication with the system via a network comprising hardware and/or software configured to allow a transaction account owner, a user, and/or the like, access to the health records system 115. The user device may comprise any suitable device that is configured to allow a user to communicate with a network and the health records system 115. The user device may include, for example, a personal computer, personal digital assistant, cellular phone, tablet, kiosk, and/or the like and may allow a user to transmit biometric information, voice communications, and/or the like.

In various embodiments, a health records management system 115 may provide access to a user 105 interfacing with system 115 by way of a client 110. Health records management system 115 may be a partially or fully integrated system comprised of various subsystems, modules and databases. Client 110 comprises any hardware and/or software suitably configured to facilitate entering, accessing, requesting, retrieving, updating, analyzing, and/or modifying data. The data may include health records (e.g., patient information, provider information, medical procedure information, clinical information, diagnostic information, immunization records, prescription information, family information, genetic information, and/or the like), or any other suitable information discussed herein.

Client 110 includes any device (e.g., a computer), which communicates, in any manner discussed herein, with health records management system 115 via any network or protocol discussed herein. Browser applications comprise Internet browsing software installed within a computing unit or system to conduct online communications and transactions. These computing units or systems may take the form of personal computers, mobile phones, personal digital assistants, mobile email devices, laptops, notebooks, hand-held computers, portable computers, tablets, kiosks, and/or the like. Practitioners will appreciate that client 110 may or may not be in direct contact with health records management system 115. For example, client 110 may access the services of health records management system 115 through another server, which may have a direct or indirect connection to Internet server 125. Practitioners will further recognize that client 110 may present interfaces associated with a software application or module that are provided to client 110 via application graphical user interfaces (GUIs) or other interfaces and are not necessarily associated with or dependent upon Internet browsers or internet specific protocols.

User 105 may communicate with health records management system 115 through a firewall 120, for example to help ensure the integrity of health records management system 115 components. Internet server 125 may include any hardware and/or software suitably configured to facilitate communications between the client 110 and one or more health records management system 115 components.

Firewall 120, as used herein, may comprise any hardware and/or software suitably configured to protect health records management system 115 components from users of other networks. Firewall 120 may reside in varying configurations including stateful inspection, proxy based and packet filtering, among others. Firewall 120 may be integrated as software within Internet server 125, or another system 115 component, or may reside within another computing device or may take the form of a standalone hardware component.

Authentication server 130 may include any hardware and/or software suitably configured to receive authentication credentials, encrypt and decrypt credentials, authenticate credentials, and/or grant access rights according to pre-defined privileges associated with the credentials. Authentication server 130 may grant varying degrees of application and/or data level access to users based on information stored within authentication database 135 and user database 140. Application server 142 may include any hardware and/or software suitably configured to serve applications and data to a connected client 110.

In accordance with various embodiments, health records management system 115 is usable to: register and/or pre-register consumers for access to the system; provide consumers and healthcare providers access to health care records; generate health service reminders and/or notifications, for example immunization reminders; deliver data to, retrieve data from, and/or transfer data between one or more states, healthcare providers, and/or consumers; and/or the like. Continuing to reference FIG. 1, health records management system 115 utilizes and/or allows communication with a primary database 150, and with various other databases, tools, UIs and systems, for example external systems and databases 160. Such systems include, for example, state immunization registries, healthcare provider systems, third-party health records management systems (for example, the "Health Vault" product offered by Microsoft Corporation), and/or the like.

Health records management system 115 components may be interconnected and communicate with one another to allow for a completely integrated health records management system.

In various embodiments, certain health records management system 115 module(s) 145 are software modules configured to enable online functions such as sending and receiving messages, receiving query requests, configuring responses, dynamically configuring user interfaces, requesting data, receiving data, displaying data, executing complex processes, calculations, forecasts, mathematical techniques, workflows and/or algorithms, prompting user 105, verifying user responses, authenticating the user, initiating health records management system 115 processes, initiating other software modules, triggering downstream systems and processes, encrypting and decrypting, and/or the like. Additionally, health records management system 115 modules may include any hardware and/or software suitably configured to receive requests from client 110, for example via Internet server 125 and application server 142. It will be appreciated that, while module 145 is illustrated as a single module in FIG. 1, in various embodiments components of health records management system 115 (and/or functionality thereof) may be combined into fewer modules or components, or alternatively, divided into additional modules and/or components.

Health records management system 115 modules may be further configured to process requests, execute transactions, construct database queries, and/or execute queries against databases within system 115 (e.g., database 150), external data sources and/or temporary databases. In various embodiments, one or more health records management system 115 modules may be configured to execute application programming interfaces in order to communicate with a variety of messaging platforms, such as email systems, wireless communications systems, mobile communications systems, multimedia messaging service ("MMS") systems, short messaging service ("SMS") systems, and the like.

Health records management system 115 modules 145 may be configured to exchange data with other systems and application modules, for example, a state immunization registry, and/or the like. In various embodiments, health records management system 115 modules 145 may be configured to interact with sub-modules, other systems, or components thereof to perform complex calculations, retrieve additional data, format data into reports, create XML representations of data, construct markup language documents, construct, define or control UIs, and/or the like. Moreover, health records management system 115 modules may reside as standalone systems or tools, or may be incorporated with the application server 142 or any other health records management system 115 component as program code. As one of ordinary skill in the art will appreciate, health records management system 115 modules may be logically or physically divided into various subcomponents, such as a workflow engine configured to evaluate predefined rules and to automate processes.

In addition to the components described above, health records management system 115 may further include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; a plurality of databases; a network interface for communicating with external electronic devices; and/or the like.

As will be appreciated by one of ordinary skill in the art, one or more health records management system 115 components may be embodied as a customization of an existing system, an add-on product, upgraded software, a stand-alone system (e.g., kiosk), a distributed system, a method, a data processing system, a device for data processing, and/or a computer program product. Accordingly, individual health records management system 115 components may take the form of an entirely software embodiment, an entirely hardware embodiment, or an embodiment combining aspects of both software and hardware. Furthermore, individual health records management system 115 components may take the form of a computer program product on a computer-readable storage medium having computer-readable program code means embodied in the storage medium. Any suitable computer-readable storage medium may be utilized, including magnetic storage devices (e.g., hard disks), optical storage devices, (e.g., DVD-ROM, CD-ROM, etc.), electronic storage devices (e.g., flash memory), and/or the like.

As used herein, "computer-readable storage medium" does not include transitory phenomena such as propagating electromagnetic signals. The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

Client 110 may include an operating system (e.g., Windows, UNIX, Linux, Solaris, MacOS, iOS, Android, Windows Mobile OS, Windows CE, Palm OS, Symbian OS, Blackberry OS, J2ME, etc.) as well as various conventional support software and drivers typically associated with mobile devices and/or computers. Client 110 may be in any environment with access to any network, including both wireless and wired network connections. In various embodiments, access is through a network or the Internet through a commercially available web-browser software package. Client 110 and health records management system 115 components may be independently, separately or collectively suitably coupled to the network via data links which include, for example, a connection to an Internet Service Provider (ISP) over the local loop as is typically used in connection with standard wireless communications networks and/or methods, such as modem communication, cable modem, satellite networks, ISDN, digital subscriber line (DSL), and/or the like. In various embodiments, any portion of client 110 may be partially or fully connected to a network using a wired ("hard wire") connection. As those skilled in the art will appreciate, client 110 and/or any of the system components may include wired and/or wireless portions.

In various embodiments, components, modules, and/or engines of health records management system 115 may be implemented as micro-applications or micro-apps. Micro-apps are typically deployed in the context of a mobile operating system, including for example, a Palm mobile operating system, a Windows mobile operating system, an Android operating system, Apple iOS, a Blackberry operating system, and the like. The micro-app may be configured to leverage the resources of the larger operating system and associated hardware via a set of predetermined rules which govern the operations of various operating systems and hardware resources. For example, where a micro-app desires to communicate with a device or network other than the mobile device or mobile operating system, the micro-app may leverage the communication protocol of the operating system and associated device hardware under the predetermined rules of the mobile operating system. Moreover, where the micro-app desires an input from a user, the micro-app may be configured to request a response from the operating system which monitors various hardware components and then communicates a detected input from the hardware to the micro-app.

Internet server 125 may be configured to transmit data to client 110, for example within markup language documents. "Data" may include encompassing information such as commands, messages, transaction requests, queries, files, data for storage, and/or the like in digital or any other form. Internet server 125 may operate as a single entity in a single geographic location or as separate computing components located together or in separate geographic locations. Further, Internet server 125 may provide a suitable web site or other Internet-based graphical user interface, which is accessible by users (such as user 105). In various embodiments, Microsoft Internet Information Server (IIS), Microsoft Transaction Server (MTS), and Microsoft SQL Server, are used in conjunction with a Microsoft operating system, Microsoft NT web server software, a Microsoft SQL Server database system, and a Microsoft Commerce Server. In various embodiments, the well-known "LAMP" stack (Linux, Apache, MySQL, and PHP/Perl/Python) are used to enable health records management system 115. Additionally, components such as Access or Microsoft SQL Server, Oracle, Sybase, InterBase, etc., may be used to provide an Active Data Object (ADO) compliant database management system. In various exemplary embodiments, components of health records management system 115 may comprise and/or utilize a HIPPA-compliant cloud computing resource, for example the Elastic Compute Cloud service offered by Amazon.com, and/or offerings from Rackspace.com, VMware, Windows Azure, and/or the like.

Like Internet server 125, application server 142 may communicate with any number of other servers, databases and/or components through any means known in the art. Further, application server 142 may serve as a conduit between client 110 and the various systems and components of health records management system 115. Internet server 125 may interface with application server 142 through any means known in the art including a LAN/WAN, for example. Application server 142 may further invoke software modules, such as system module(s) 145, automatically or in response to user 105 requests.

Any of the communications, inputs, storage, databases or displays discussed herein may be facilitated through a web site having web pages. The term "web page" as it is used herein is not meant to limit the type of documents and applications that may be used to interact with the user. For example, a typical web site may include, in addition to standard HTML documents, various forms, Java applets, JavaScript, active server pages (ASP), common gateway interface scripts (CGI), Flash files or modules, FLEX, ActionScript, extensible markup language (XML), dynamic HTML, cascading style sheets (CSS), helper applications, plug-ins, and/or the like.

Continuing to reference FIG. 1, illustrated are databases that are included in various embodiments. An exemplary list of various databases used herein includes: an authentication database 135, a user database 140, primary database 150 and/or other databases that aid in the functioning of the system. As practitioners will appreciate, while depicted as separate and/or independent entities for the purposes of illustration, databases residing within health records management system 115 may represent multiple hardware, software, database, data structure and networking components. Furthermore, embodiments are not limited to the databases described herein, nor do embodiments necessarily utilize each of the disclosed databases.

Authentication database 135 may store information used in an authentication process, for example user identifiers, passwords, access privileges, user preferences, user statistics, and the like. User database 140 maintains user information and credentials for health records management system 115 users (e.g., user 105).

In various embodiments, primary database 150 is a data repository that may be configured to store a wide variety of comprehensive data for health records management system 115. While depicted as a single logical entity in FIG. 1, those of skill in the art will appreciate that primary database 150 may, in various embodiments, consist of multiple physical and/or logical data sources. In various embodiments, primary database 150 stores one or more of consumer name, date of birth, street address, phone number, email address, password, security question and answer, gender, consumer relationship information (e.g., spouse, parent, child, guardian, dependent, etc.), immunization type and vaccine family information, immunization date information, administering provider, risk factors, age appropriate schedule of immunizations due or past due or next due, vaccine status (public vs. private), narrative content of an informational nature, and/or the like.

Any databases discussed herein may include relational, hierarchical, graphical, or object-oriented structure and/or any other database configurations. Common database products that may be used to implement the databases include DB2 by IBM (Armonk, NY), various database products available from Oracle Corporation (Redwood Shores, CA), Microsoft Access or Microsoft SQL Server by Microsoft Corporation (Redmond, Washington), MySQL by MySQL AB (Uppsala, Sweden), Ehcache, Couchbase, VoltDB, Versant, Hazelcast, or any other suitable database product, for example a persistent and distributed in-memory database product. Moreover, the databases may be organized in any suitable manner, for example, as data tables or lookup tables. Each record may be a single file, a series of files, a linked series of data fields or any other data structure. Association of certain data may be accomplished through any desired data association technique such as those known or practiced in the art. For example, the association may be accomplished either manually or automatically. Automatic association techniques may include, for example, a database search, a database merge, GREP, AGREP, SQL, using a key field in the tables to speed searches, sequential searches through all the tables and files, sorting records in the file according to a known order to simplify lookup, and/or the like. The association step may be accomplished by a database merge function, for example, using a "key field" in pre-selected databases or data sectors. Various database tuning steps are contemplated to optimize database performance. Examples include distributing data elements to grid memory, optimizing partitioning of memory objects to process, indexing frequently used files and placing on separate file systems to reduce Input/Output ("I/O") bottlenecks.

One skilled in the art will also appreciate that, for security reasons, any databases, systems, devices, servers or other components of health records management system 115 may consist of any combination thereof at a single location or at multiple locations, wherein each database or system includes any of various suitable security features, such as firewalls, access codes, encryption, decryption, compression, decompression, and/or the like.

The systems and methods may be described herein in terms of functional block components, screen shots, optional selections and various processing steps. It should be appreciated that such functional blocks may be realized by any number of hardware and/or software components configured to perform the specified functions. For example, the system may employ various integrated circuit components, e.g., memory elements, processing elements, logic elements, look-up tables, and the like, which may carry out a variety of functions under the control of one or more microprocessors or other control devices. Similarly, the software elements of the system may be implemented with any programming or scripting language such as C, C++, C#, Java, JavaScript, Flash, ActionScript, FLEX, VBScript, Macromedia Cold Fusion, COBOL, Microsoft Active Server Pages, assembly, PERL, SAS, PUP, awk, Python, Visual Basic, SQL Stored Procedures, PL/SQL, any UNIX shell script, extensible markup language (XML), and/or the like, with the various algorithms being implemented with any combination of data structures, objects, processes, routines or other programming elements. Further, it should be noted that the system may employ any number of conventional techniques for data transmission, signaling, data processing, network control, and the like. Still further, the system may be used to detect or prevent security issues with a client-side scripting language, such as JavaScript, VBScript and/or the like.

Software elements may be loaded onto a general purpose computer, special purpose computer, or other programmable data processing apparatus to produce a machine, such that the instructions that execute on the computer or other programmable data processing means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified herein or in flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions. Further, illustrations of the process flows and the descriptions thereof may make reference to user windows, web pages, web sites, web forms, prompts, etc. Practitioners will appreciate that the illustrated steps described herein may comprise any number of configurations including the use of windows, web pages, web forms, popup windows, prompts and/or the like. It should be further appreciated that the multiple steps as illustrated and described may be combined into single web pages and/or windows but have been expanded for the sake of simplicity. In other cases, steps illustrated and described as single process steps may be separated into multiple web pages and/or windows but have been combined for simplicity.

With continued reference to FIG. 1, in various embodiments, user 105 logs onto an application (e.g., a module) and Internet server 125 may invoke an application server 142. Application server 142 invokes logic in health records management system 115 modules by passing parameters relating to user's 105 requests for data. Health records management system 115 manages requests for data from health records management system 115 modules and/or communicates with internal and/or external components. Transmissions between user 105 and Internet server 125 may pass through a firewall 120 to help ensure the integrity of health records management system 115 components. Practitioners will appreciate that exemplary embodiments may incorporate any number of security schemes or none at all. In various embodiments, Internet server 125 receives requests from client 110 and interacts with various other health records management system 115 components to perform tasks related to requests from client 110.

Internet server 125 may invoke an authentication server 130 to verify the identity of user 105 and assign roles, access rights and/or permissions to user 105. For example, a user 105 may be a consumer, a health records provider, a state administrator, and so forth, and the rights, roles, permissions, and access thereof may be customized and/or limited, as desired. In order to control access to the application server 142 or other components of health records management system 115, Internet server 125 may invoke an authentication server 130 in response to user 105 submissions of authentication credentials received at Internet server 125. In response to a request to access health records management system 115 being received from Internet server 125, Internet server 125 determines if authentication is required and transmits a prompt to client 110. User 105 enters authentication data at client 110, which transmits the authentication data to Internet server 125. Internet server 125 passes the authentication data to authentication server 130 which queries the user database 140 for corresponding credentials. In response to user 105 being authenticated, user 105 may access various applications and their corresponding data sources.

Figure 2A:
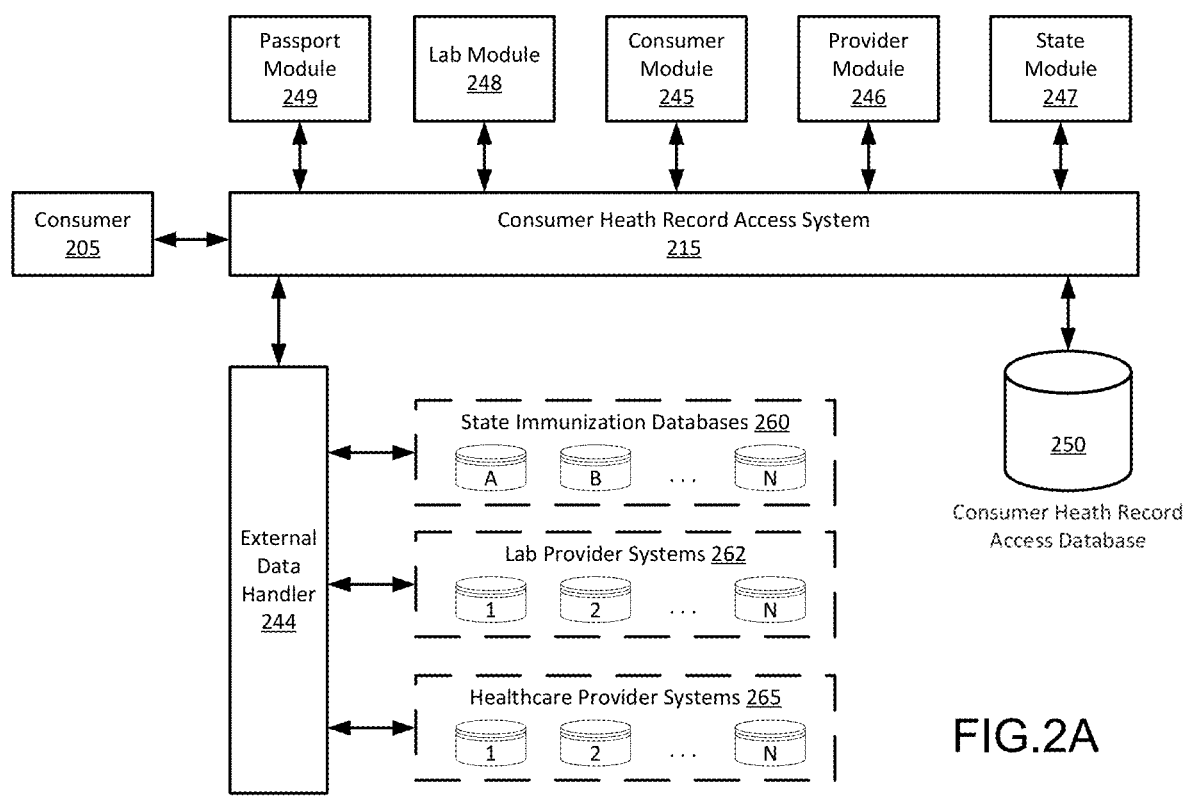
FIG. 2A is a block diagram illustrating exemplary consumer health record access system components, in accordance with various embodiments.
Figure 2B:
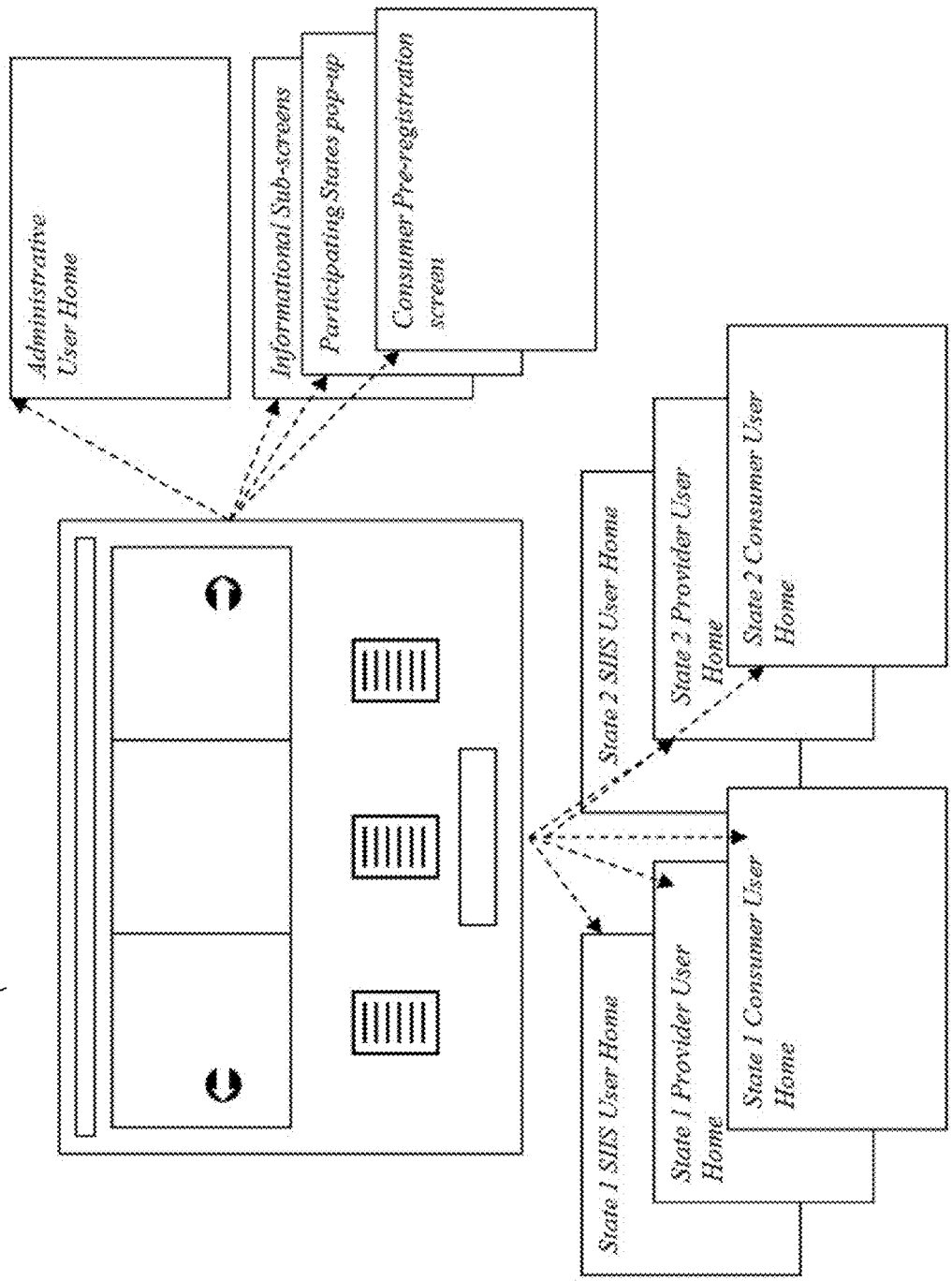
FIG. 2B illustrates exemplary screen layouts of an exemplary consumer health record access system in accordance with various embodiments.

With reference now to FIGS. 2A and 2B, in various embodiments, a health records management system 115, for example consumer health record access system 215, provides comprehensive access to immunization records, for example by and among states, healthcare providers, and consumers. As opposed to prior systems wherein consumers were required to obtain immunization records from healthcare providers and/or directly from the state, consumer health record access system 215 allows consumers to access immunization records from and/or deliver immunization records to one or more state immunization registries. Additionally, many states previously required that a consumer create a read-only account with a state immunization registry before viewing immunization records; in contrast, via use of consumer health record access system 215, consumers can both retrieve immunization records from a state as well as provide immunization records to a state (for example, a consumer can provide immunization records from State A to State B after the consumer moves from State A to State B).

System 115 may be computer based, and may comprise a processor, a tangible non-transitory computer-readable memory, and/or a network interface, along with other suitable system software and hardware components. Instructions stored on the tangible non-transitory memory may allow system 115 to perform various functions, as described herein. In various embodiments, the application server 115 and/or consumer heath record access system service (i.e., service 215) may be configured as a central network element or hub to access various systems, engines, and components of system 115.

In various exemplary embodiments, consumer health record access system 215 comprises consumer module 245, provider module 246, state module 247, lab module 248, passport module 248, external data handler 244, and consumer health record access database 250. Consumer health record access system 215 may interface with and/or be capable of communication with one or more external data sources or databases such as, for example, state immunization databases 260 (e.g. State A, State B, State C, . . . State N), lab provider systems 262 (e.g., System 1, System 2, System 3, . . . System N), healthcare provider systems 265 (e.g. System 1, System 2, System 3 . . . System N), consumers/users 205, and/or the like. Consumer health record access system 215 may comprise various interactive web pages, software modules, and/or the like, for example as illustrated in FIG. 2B.

Consumer module 245 is configured for use by consumers. In various exemplary embodiments, consumer module 245 is configured to support registering consumers for an account, pending authentication/approval by a participating healthcare provider. Consumer module 245 provides a consumer with timely and relevant public and personal health information including but not limited to immunization-related information. Consumer module 245 also provides consumers with a mechanism to "cohort" (group together) family members under a single consumer account for the purposes of conveniently obtaining copies of their immunization records, for example once each family member is authenticated/approved by a participating healthcare provider.

In certain exemplary embodiments, consumer module 245 provides a consumer with an overview of all recorded immunizations for each approved family member. The source for the recorded immunization data may be any suitable source, but in various embodiments, the data source is the participating state(s) immunization information system or "registry".

Consumer module 245 is configured to provide a consumer with an immunization forecast (a schedule of recommended immunizations that are coming due, now due, or past due). The forecast may be generated based on any suitable factors. In certain embodiments, the forecast is determined in accordance with national recommendations from the U.S. Centers for Disease Control and Prevention, and/or from state-specific immunization schedule requirements.

Consumer module 245 is configured to provide a consumer with one or more electronic copies (for example, in PDF format) of an immunization record (for example, an immunization registry-based record) for each authenticated/approved family member. The records are formatted to conform in content and appearance, according to state-specific requirements.

Consumer module 245 provides a consumer with a feedback mechanism (for example, via a web forum), allowing the collection of user-experience, testimonials, and suggestions, and comprising a vehicle for the establishment of a community-of-users. Additionally, consumer module 245 provides a consumer with an automated reminder function that alerts the consumer (via various modalities) to immunizations that are coming due, now due, or past due for any authenticated/approved family member.

Yet further, consumer module 245 provides a consumer with a mechanism to share, at the consumer's discretion, copies of any of his or her immunization records with third parties (e.g., healthcare providers, a personal health record system, and/or the like) that can receive data formatted according to the federal BlueButton+ standards (a body of standards promulgated and maintained by the U.S. Department of Health and Human Services).

Consumer module 245 provides a consumer with the ability to report to various authorities any perceived discrepancy between their record content (for example, immunization record content) and their personal knowledge (or other source documentation) of their complete immunization history; this allows other authorized entities (e.g., participating healthcare provider) to investigate and resolve discrepancies. Consumer module 245 also provides consumers with non-immunization-related content and functionality, for example personal/household risk assessments, electronic connections with other public health program agencies, preventive health services information, and opportunities to volunteer for participation in state-specific public health oriented surveys, studies, and trials. Consumer module 245 may also provide program, provider, or services locator functionality, or interface with downloadable application(s) for use with smartphone devices and tablet computers.

Consumer module 245 provides a consumer with age-appropriate anticipatory guidance materials for childhood-related health risks, with a look-up feature for participating healthcare providers, and with the ability to obtain electronic copies of immunization records from any state that participates with consumer health record access system 215 (and for which the consumer and their family member(s) have been authenticated and approved in the respective states).

With continued reference to FIG. 2A, provider module 246 is configured for use by healthcare providers. In various exemplary embodiments, provider module 246 allows providers to register and authenticate/approve consumers who request an account, including family members for which he or she requests records access.

Provider module 246 allows providers to look-up consumers who have registered (pending authentication/approval) and to authenticate and approve or reject consumer requests for an account. Moreover, provider module 246 provides providers with relevant public health and personal health information applicable to immunizations as well as other topics.

In certain exemplary embodiments, provider module 246 provides providers with peer-reviewed tools, guidance documents, and patient educational materials pertinent to immunizations, captures demographic and practice-specific information specific to participating providers, and allows provider look-up of view-only records within the state-specific Immunization Information System to which they have been granted approved access.

Provider module 246 may be configured to allow providers to deactivate (suspend) records access permission for any approved consumer or family member. Provider module 246 provides providers with metrics regarding the nature and frequency of consumer health record access system 215 usage by consumers for which the provider has authenticated/approved access.

In various exemplary embodiments, provider module 246 provides providers a user feedback mechanism (for example a web forum, chat room, and/or the like) to allow sharing of comments, suggestions, testimonials, etc., and to create a community of users. Additionally, provider module 246 provides providers a mechanism by which consumers can submit reports of record discrepancies, for example via transmissions using the federal BlueButton+ data exchange standards. Moreover, provider module 246 allows providers to receive the results of consumer risk assessments and other consumer-initiated health information from consumers that voluntarily seek to provide such information to their healthcare provider.

Provider module 246 can provide providers a mechanism to view alerts and other information posted by authorities at the respective state immunization program or registry. Provider module 246 may be configured with a remote lookup capability wherein a provider may view, in read only mode, immunization records for any resident of a state, even if such resident is not a patient of the provider.

With continued reference to FIG. 2A, state module 247 is configured for use by state representatives. For example, state module 247 allows state administrative representatives to create new provider accounts, allows state administrative representatives to deactivate (suspend) previously created provider accounts, and allows state administrative representatives to deactivate (suspend) the accounts of any previously authenticate/approved consumer or family member.

In various exemplary embodiments, state module 247 allows state administrative representatives to create and post informational content (e.g., alerts, guidance, public health information, etc.) to a state-specific consumer web page or provider web page. Additionally, state module 247 allows state administrative representatives to view various metrics summarizing system performance and/or pertaining to system usage by consumer and provider account-holders.

In some exemplary embodiments, state module 247 allows state administrative representatives to communicate via e-mail with consumer and provider account-holders, to manage various configurable settings governing state-specific application behavior and functionality, and to receive transmissions from account holders sent via BlueButton+ standards. State module 247 may be configured with analytics capabilities to allow state representatives to visualize trending, provider referral details, and otherwise analyze system use by consumers in their state. State module 247 may also comprise and/or be configured with forecasting tools, for example in order to evaluate potential future immunization needs or other modeled public health requirements or outcomes.

With continued reference to FIG. 2A, lab module 248 is configured for use by lab providers. In various exemplary embodiments, lab module 248 allows lab providers to register and authenticate/approve consumers who request an account, including healthcare providers and/or family members for which he or she requests records access.

Lab module 248 allows providers to look-up consumers who have registered (pending authentication/approval) and to authenticate and approve or reject consumer requests for an account. Moreover, lab module 248 provides providers with relevant public health and personal health information applicable to lab work and immunizations as well as other topics.

In certain exemplary embodiments, lab module 248 provides lab providers with peer-reviewed tools, guidance documents, and patient educational materials pertinent to lab work, captures demographic and practice-specific information specific to participating providers, and allows provider look-up of view-only records within the state-specific healthcare database systems (e.g., healthcare information exchanges) which they have been granted approved access.

Lab module 248 may be configured to allow providers to deactivate (suspend) records access permission for any approved consumer, healthcare provider, or family member. Lab module 248 provides providers with metrics regarding the nature and frequency of consumer health record access system 215 usage by consumers for which the provider has authenticated/approved access.

In various exemplary embodiments, lab module 248 provides providers a user feedback mechanism (for example a web forum, chat room, and/or the like) to allow sharing of comments, suggestions, testimonials, etc., and to create a community of users. Additionally, provider module 246 provides providers a mechanism by which consumers can submit reports of record discrepancies, for example via transmissions using the federal BlueButton+ data exchange standards. Moreover, lab module 248 may enable providers to receive the results of consumer risk assessments and other consumer-initiated health information from consumers that voluntarily seek to provide such information to their healthcare provider.

Lab module 248 can provide providers a mechanism to view alerts and other information posted by authorities at the respective state immunization program or registry. Lab module 248 may be configured with a remote lookup capability wherein a provider may view, in read only mode, immunization records for any resident of a state, even if such resident is not a patient of the provider.

In various embodiments and with continued reference to FIG. 2A, passport module 249 is configured to compile consumer health records to generate passport report data and to deliver the passport report data to passport data users. The passport module may compile data from state immunization databases 260, lab provider systems 262, and healthcare provider systems 265 to generate the passport report data. The system may store the passport report data in consumer health record access database 250. In various embodiments, the passport report data may comprise a record of immunizations associated with a consumer health record, immunization-related information, lab related information (e.g., test results, test dates, etc.), and/or the like.

Passport module 249 may comprise an application program interface configured to provide a programmatic interface to any of the set of system 215 services, components, modules, and/or engines. In various embodiments, the passport module 249 may be configured to generate a matrix barcode such as, for example, a QR code comprising the passport report data. The passport module 249 may be configured to enable the matrix barcode comprising the passport report data to be displayed on a user device. In this regard, the passport module 249 may enable transfer of passport report data to third parties which may read the displayed matrix barcode. For example an entertainment venue may request the passport report data associated with a consumer who whishes to enter the venue. System 215 may receive the passport report data request and, in response, compile the database data to generate the passport report data. The system may pass the passport report data to the venue via the API or the matrix barcode.

Consumer health record access database 250 stores information utilized by consumer health record access system 215, for example information similar to information stored in primary database 150.

In various exemplary embodiments, consumer health record access system 215 is configured to provide bi-directional Health Level 7 (HL7) messaging capability to state immunization registries and health care providers.

In various exemplary embodiments, consumer health record access system 215 is configured to provide a state-specific or state-required immunization report or certification form, for example as illustrated in FIG. 2F. Such reports may take the form of official state forms. Stated another way, consumers can access immunization documentation in both informal (i.e., report) form, as well as in formal (i.e., official state documentation) form. In this manner, states can simplify access to and distribution of official state immunization information and forms to consumers.

In various exemplary embodiments, consumer health record access system 215 is configured to provide state immunization administrators with a set of pre-defined and/or customizable web pages with communication and/or messaging capabilities. In this manner, state subscribers to consumer health record access system 215 can communicate to consumers in their state, for example to provide news, alerts, and so forth.

Figure 2E:
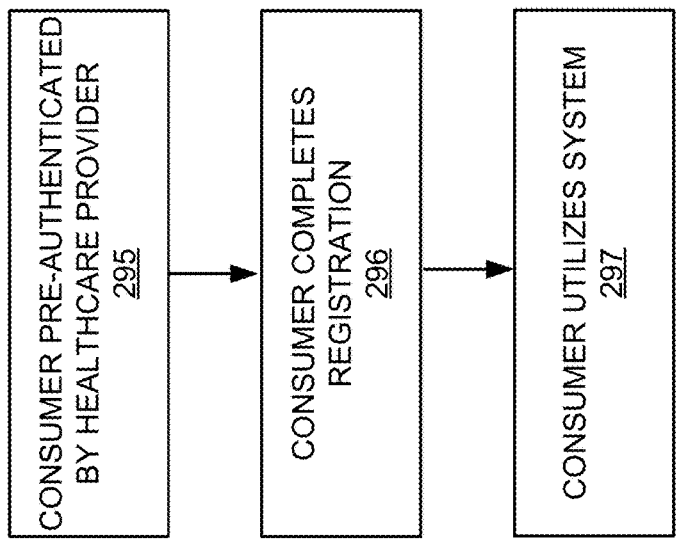
FIGS. 2C through 2E illustrate methods of registering a consumer in an exemplary consumer health record access system in accordance with various embodiments.
Figure 2D:
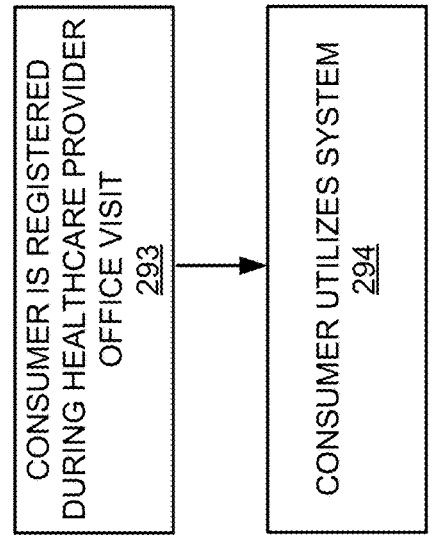
Figure 2C:
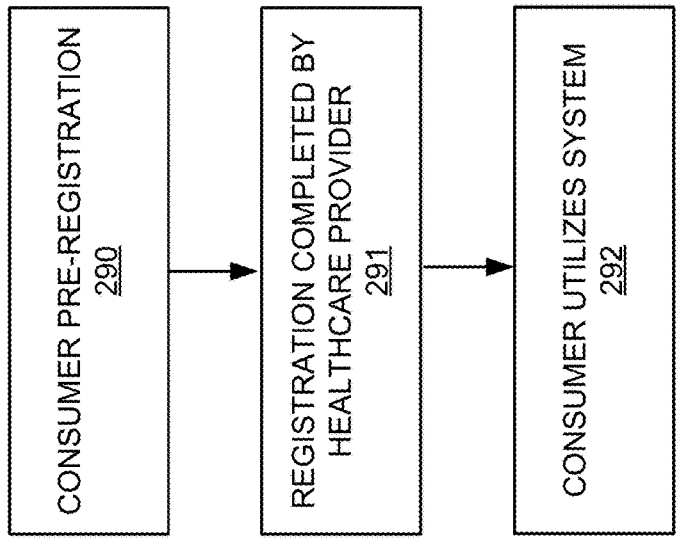

With reference now to FIG. 2C, in an exemplary embodiment a consumer pre-registers for access to consumer health record access system 215 (step 290). The consumer registration is completed during an office visit with a healthcare provider (step 291). The consumer may thereafter utilize the features of consumer health record access system 215 (step 292).

Turning now to FIG. 2D, in other exemplary embodiments, consumer registration is initiated and completed during an office visit with a healthcare provider (step 293). The consumer may thereafter utilize the features of consumer health record access system 215 (step 294).

Turning now to FIG. 2E, in other exemplary embodiments, a consumer is pre-authenticated by a healthcare provider (step 295). The consumer later completes the registration process (step 296). The consumer may thereafter utilize the features of consumer health record access system 215 (step 297).

"Registration" and/or "pre-registration" as utilized herein may be via any suitable method or system as known in the art, for example via username and password, welcome email and PIN, or other suitable authentication system.

In various exemplary embodiments, consumer health record access system 215 is configured to provide state-specific or state-required immunization reports or certification forms, for example as illustrated in FIG. 2F. Such reports may take the form of official state forms. Stated another way, consumers can access immunization documentation in both informal (i.e., report) form, as well as in formal (i.e., official state documentation) form. In this manner, states can simplify access to and distribution of official state immunization information and forms to consumers.

In various exemplary embodiments, when a consumer moves from State A to State B, the consumer will retain access in consumer health record access system 215 to records from State A, even after being authenticated into new State B. In this manner, centralized access to immunization records is facilitated. Via consumer health record access system 215, a consumer may also share records among states; i.e., a consumer may provide State B immunization information to State A to update the records of State A. Yet further, via consumer health record access system 215, a consumer may instruct that immunization records be provided, in a standardized format and/or protocol such as BlueButton+, to any external record acceptor (for example, healthcare providers, Microsoft Health Vault, and/or the like).

In various exemplary embodiments, consumer health record access system 215 checks immunization records in consumer health record access database 250 on a regular basis (for example, daily, weekly, bi-weekly, monthly, and so forth). Consumer health record access system 215 may be configured to send automated reminders to consumers and/or health care providers regarding upcoming scheduled immunizations, past due immunizations, supplementary recommended immunizations due to public health alerts, and/or the like.

In certain exemplary embodiments, consumer health record access system 215 provides "cohorting" capabilities to a consumer. In these embodiments, a particular consumer (e.g., a parent or guardian) may view and/or access immunization information for other consumers (e.g., a child or ward). In this manner, household immunization information may be centralized, facilitating improved immunization outcomes. For example, an adoptive parent may quickly determine that a particular child lacks a certain immunization previously received by other children in the same household; the parent can then schedule the suggested immunization.

In various exemplary embodiments, consumer health record access system 215 is usable to provide actionable information directly to a consumer based on at least one of the consumer's immunization history, age, gender, or risk. Consumer health record access system 215 supports inter-jurisdictional information retrieval, allowing a consumer to access his or her immunization records, either alone or in connection with the records of one of more family members, from multiple states. Consumer health record access system 215 is configured to provide seamless integration with other medical records systems, for example as found in retail health, clinical or personal health records, health information exchanges, and the like. Consumer health record access system 215 can provide consumer prevention information, screening data components, medical device integration, family pet immunization histories, and so forth.

In various exemplary embodiments, consumer health record access system 215 allows consumers to pre-register for an account, for example by specifying their desired password and e-mail address. Additionally, consumer health record access system 215 provides consumer-managed cohorting of family members. For example, consumer health record access system 215 can send requests for records access to a provider approval queue for any family member for which a consumer may request records access. Yet further, consumer health record access system 215 allows for provider-managed consumer registration/approval; this approach allows providers to optionally register and approve consumers in their healthcare setting.

In certain exemplary embodiments, consumer health record access system 215 is configured to support provider look-up of matching and/or closely matching records. For example, consumer health record access system 215 allows providers to view, within consumer health record access system 215, attributes of matching or closely matching records, for example records located through an HL7 query to a respective state immunization information system.

Consumer health record access system 215 is configured to provide immunization records reports and/or certificates. In one embodiment, consumer health record access system 215 allows consumers one generic and one or more state-specific views of immunization records that can be printed, stored, or pushed to other destinations.

Consumer health record access system 215 provides third-party consumer and provider educational information and tools. For example, consumer health record access system 215 provides ongoing access to archival and new peer-reviewed reference and educational materials targeted at consumers and providers (respectively).

In some exemplary embodiments, consumer health record access system 215 is configured with BlueButton+ capability. In this manner, consumer health record access system 215 may export copies of immunization records in the federal BlueButton+ format, enabling consumers to share their immunization records with providers and/or personal health records (PHR) service providers or software of their choosing.

Consumer health record access system 215 is configured to provide system performance metrics and analytics. This allows authorized administrative users to monitor system performance, attributes of users, system behavior and usage patterns. Additionally, consumer health record access system 215 is configured with a scalable user interface, permitting consumer health record access system 215 to be accessed and/or utilized on different devices (e.g., computer, tablet, smartphone).

Consumer health record access system 215 is interoperable with any HL7-compliant state immunization registry. In this manner, consumer health record access system 215 may be subscribed to by any state immunization registry.

Moreover, consumer health record access system 215 provides anticipatory guidance (preventive health) information for age-appropriate cohorts of children via consumer accounts, provides consumer health/household risk assessment instruments and analyses, and provides a communications exchange with various public health program areas of a topical nature.

In some exemplary embodiments, consumer health record access system 215 provides automated reminders for immunization and additional preventive health care-associated circumstances, provides provider and preventive services access and locational look-up features, and provides consumer alerting of healthcare providers to possible errors in record content.

Figure 3A:
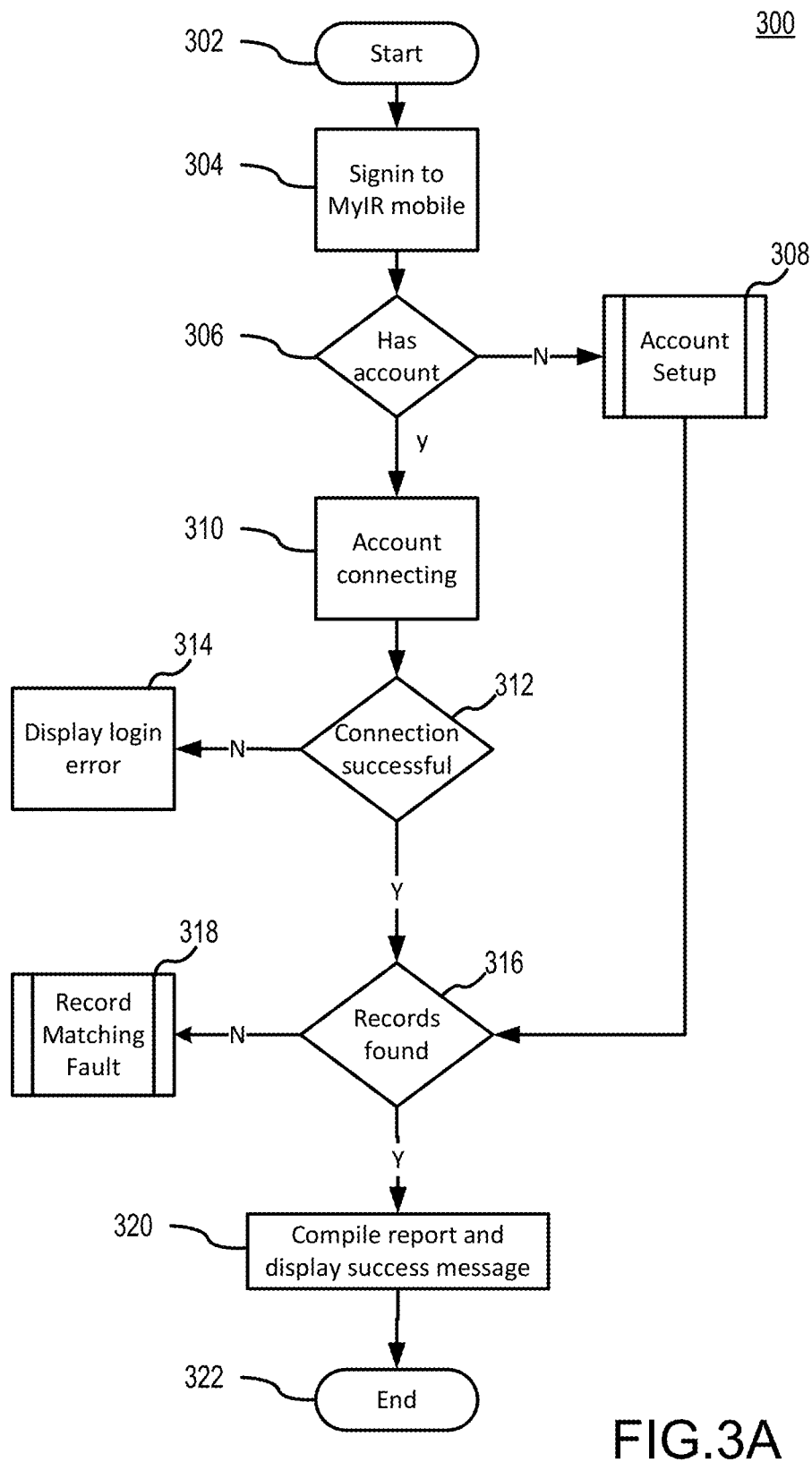
FIG. 3A illustrates a process for generating a passport report of an exemplary consumer health record access system in accordance with various embodiments.
Figure 3B:
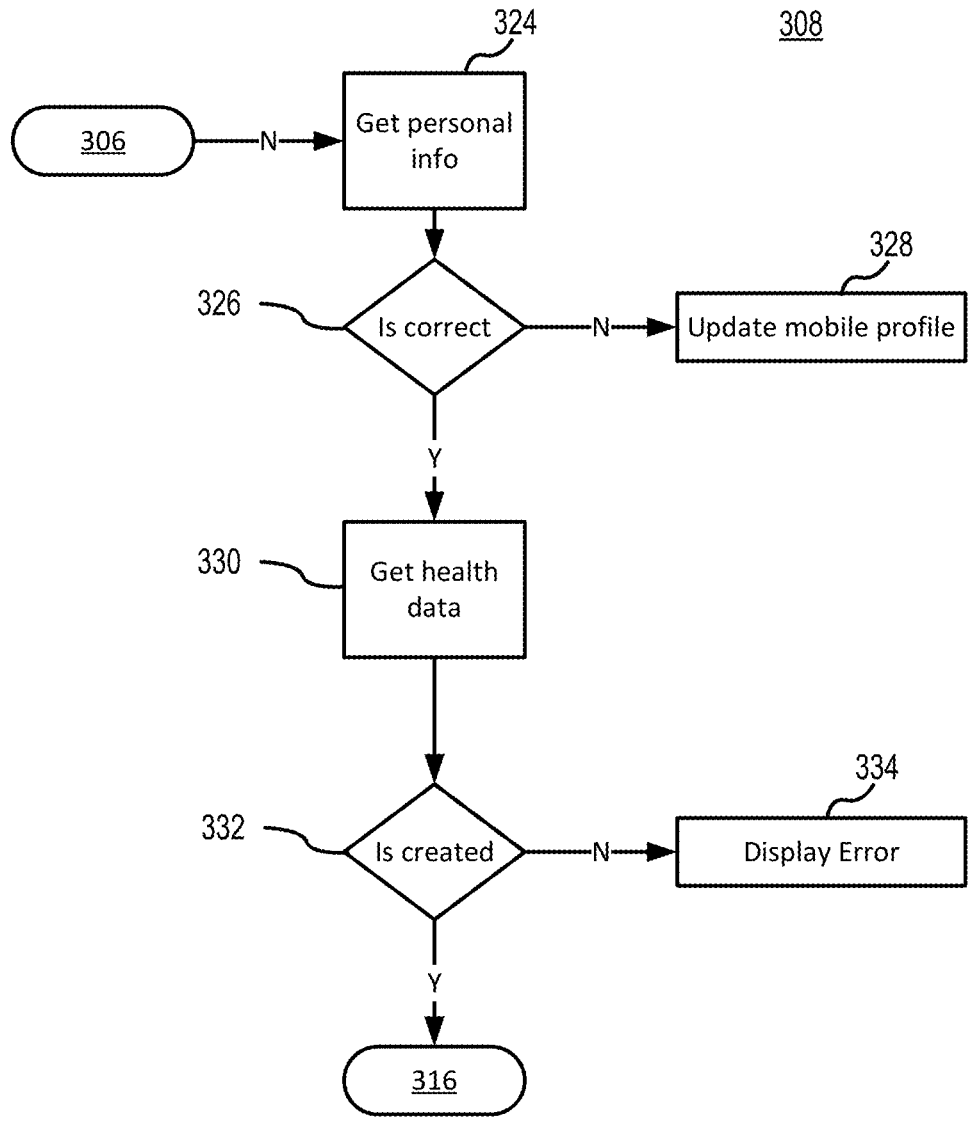
FIG. 3B illustrates an account setup process in an exemplary consumer health record access system in accordance with various embodiments.
Figure 3C:
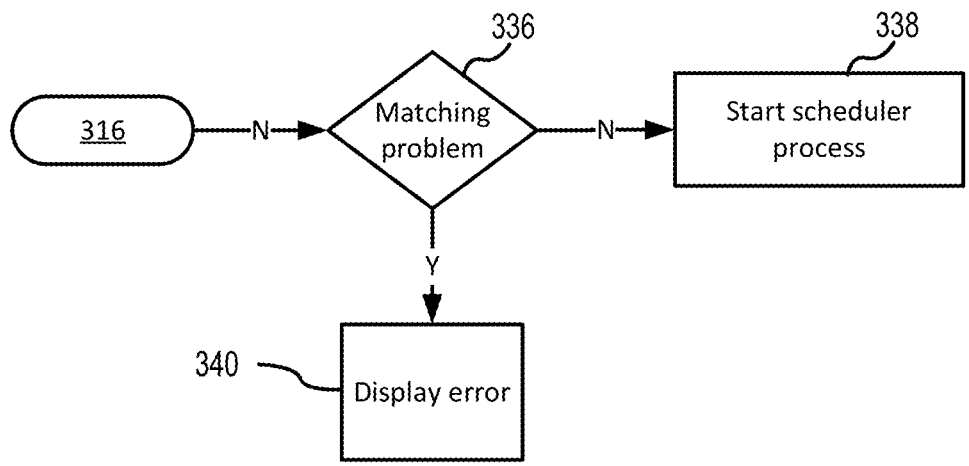
FIG. 3C illustrates a record matching fault process in an exemplary consumer health record access system in accordance with various embodiments.
Figure 4:
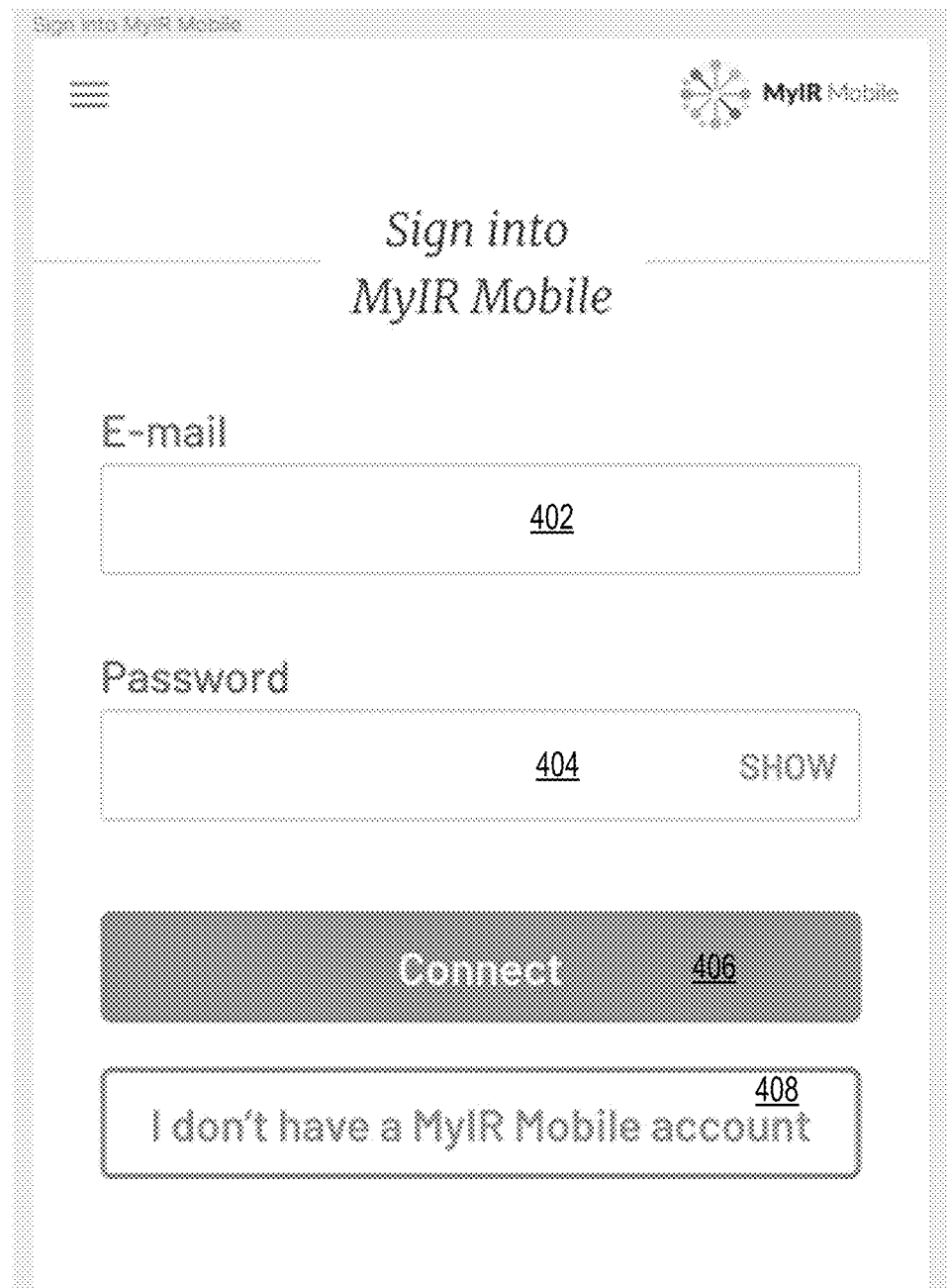
FIG. 4 illustrates a sign-in page of an exemplary consumer health record access system in accordance with various embodiments.
Figure 5:
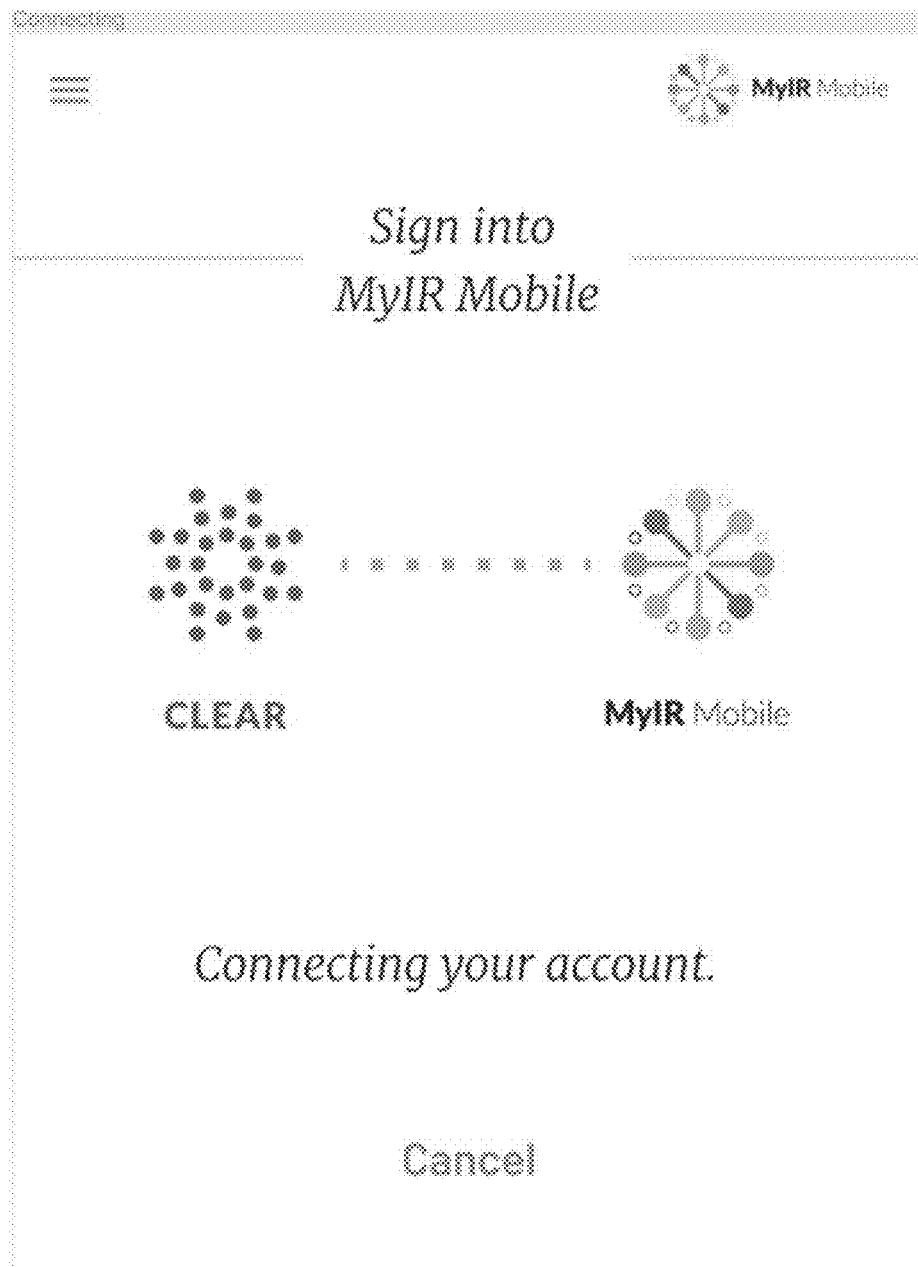
FIG. 5 illustrates a connecting account page of an exemplary consumer health record access system in accordance with various embodiments.

With additional reference to FIGS. 3A, 3B, and 3C, a process 300 for generating a passport report of system 115 is illustrated. The system may receive a request for a passport report and, in response, start process 300 (step 302). In various embodiments, the request for a passport report may be generated by a third party application. The system may receive authentication and/or sign-in information (step 304). For example, as shown in FIG. 4, the system may display a sign-in page 400 via the user device. Sign in page 400 may be configured to prompt a user to enter the sign-in information for a MyIR Mobile account. Page 400 may include one or more fields configured to receive text data. In various embodiments, the sign-in information may comprise an email address which may via an email field 402 and a password which may be received via password field 404. The system may perform and account check and determine whether an existing account associated with the sign-in information is configured in system 115 (step 306). For example, page 400 may display a connect button 406. The system may generate a connection event in response to a user interaction with the connect button 406. The system may perform the account check in response to generating the connection event.

Where no existing account is associated with the sign-in information, they system may start an account setup process 308. For example, page 400 may display an account creation button 408. The system may generate an account creation event in response to a user interaction with the account creation button 408. The system may start the account setup process 308 in response to the account creation event. In response to determining an existing account is associated with the sign-in information, the system may, the system may attempt to enable a connection between the system 215 and third party passport report data user (step 310). In various embodiments and with additional reference to FIG. 5, a connecting account page 500 of system 115 is illustrated. The system may display the connecting account page 500 in response to generating the connection event.

Figure 8:
FIG. 8 illustrates a link successful page of an exemplary consumer health record access system in accordance with various embodiments.
Figure 8:
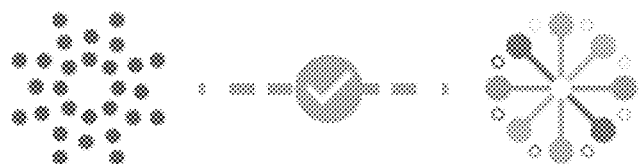

In various embodiments, the system may determine whether the connection attempt is successful (step 312). If the connection attempt fails, the system may display a login error message 314. In various embodiments, error message 314 may comprise details about the nature of the connection attempt failure. In response to a successful connection attempt, the system may determine whether a desired set of records (e.g., consumer health record access database 250 records) are associated with the account (step 316). For example, the system may perform matching between the immunization and test records associated in database 250 with the account and a requirement set of immunization and test records. Where no records are found, the system may start a record matching fault process 318. Where records are found, the system may proceed to compile the passport report data based on the matching records (step 320). In various embodiments and with reference to FIG. 8, the system may display a link successful page 800 in response to compiling the passport report data. In various embodiments, the system may transmit the passport report data to the third party application and end process 300 (step 322). For example, page 800 may be configured to include a return button 802. The system may generate a return to third party application event in response to a user interaction with the return button 802. The system may transmit the passport report data to the third party application and may command the user device to return to the third party application in response to generating the return to third party application event.

In various embodiments and with renewed reference to FIG. 3B, account setup process 308 is illustrated. The system may receive personal information data (step 324). For example, the system may receive the personal information from a third party application or may receive personal information from the user device. The personal information may include a name, a gender, a date of birth, a phone number, an email address, a mailing address, a consent to release information, and/or the like. In various embodiments, the system may transmit a request for personal information to a third party application and may receive the personal information via the API of the passport module 249.

Figure 6:
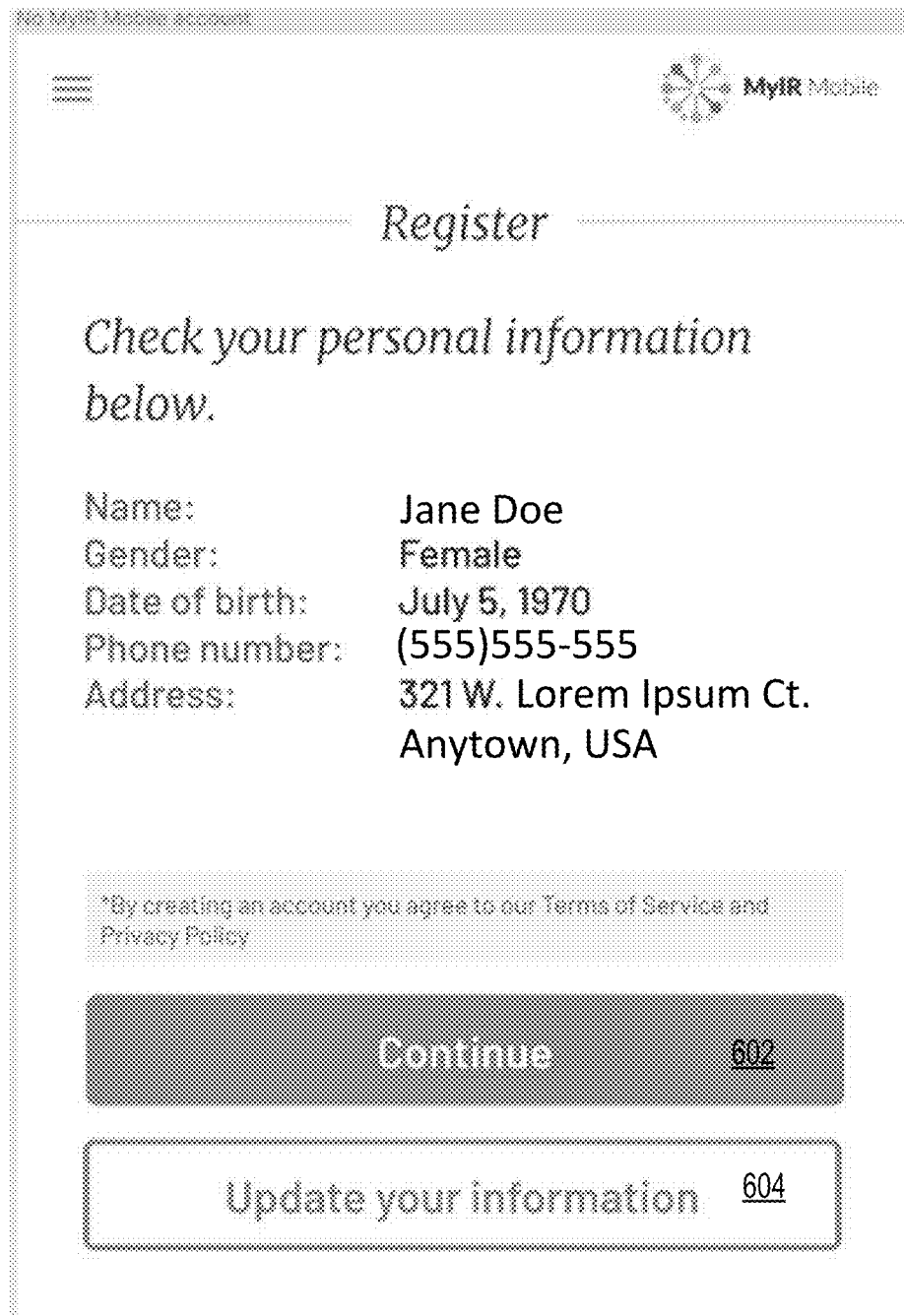
FIG. 6 illustrates a confirmation page of an exemplary consumer health record access system in accordance with various embodiments.

In various embodiments, the system may determine whether the personal information is correct (step 326). For example, as illustrated in FIG. 6, the system may display a confirmation page 600. The confirmation page 600 may display one or more elements of the personal information received in step 324 such as, for example, name, gender, date of birth, phone number, and mailing address. If the information is incorrect, they system may prompt to update the information and/or start an update profile process (step 328). For example, page 600 may display an update information button 604. The system may generate an update information event in response to a user interaction with the update information button (604). In response to generating the update information event, the system may start the update information process and thereby enable user editing of the personal information.

Figure 7:
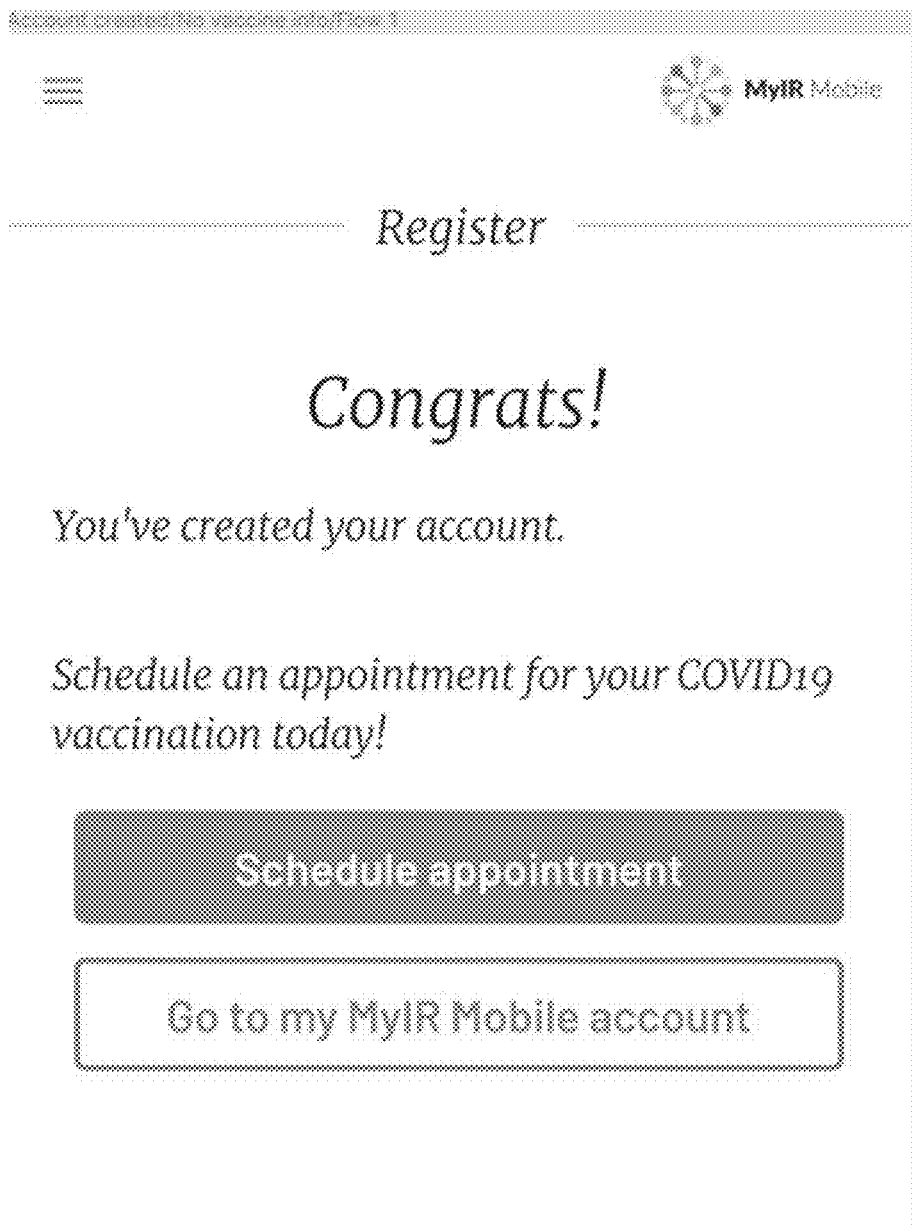
FIG. 7 illustrates an account creation success page of an exemplary consumer health record access system in accordance with various embodiments.
Figure 9:
FIG. 9 illustrates a database targeting page of an exemplary consumer health record access system in accordance with various embodiments.

If the information is correct, the system may proceed to receive external health database targeting data (step 330). In various embodiments, as shown in FIG. 9, the system may display a database targeting page 900. The system may prompt to select one or more state immunization databases 260, lab provider systems 262, and/or healthcare provider systems 265. For example, page 900 may include a state database menu 902 and a healthcare provider menu 904. For example, user may interact with the menus 902, 904 and thereby the system may receive external heal database targeting data to configure data handler 244. Step 300 may include extracting and/or ingesting health records from the databases defined by the external health database targeting data. In response to receiving the health records, the system may generate a new account associated with the health records (step 332). The system may determine whether the new account was successfully generated and associated with the health records and proceed to step 316. In various embodiments, as shown in FIG. 7, the system may display an account creation success page 700 in response to successfully generating the new account. Otherwise, the system may generate an error message (step 334). The system may display the error message via the user device.

In various embodiments and with renewed reference to FIG. 3C, record matching fault process 318 is illustrated. The system may determine whether the health records match with the requirement set of immunization and test records, the personal information, and/or the like (step 336). For example, the system may perform key field matching between the health records set and the requirements set. Where a match is unable to be determined, the system may generate an error (step 340). In various embodiments, in response to determining the health records match with the requirement set, the system may determine an unmet requirement. In response to determining an unmet requirement, the system may start a scheduler process (step 338). For example, the requirement set may include a matching record showing immunization for measles. If no health record of measles immunization is found, the system may start the scheduler process to enable scheduling of a measles immunization by a consumer at a healthcare provider. In another example, the requirement set may include a matching lab report showing a negative test for an illness having been generated within the last 30 days. If no health record newer than 30 days old showing the negative test for an illness is found, the system may start the scheduler process to enable scheduling of the test by the consumer at a lab provider.

While the present disclosure may be described in terms of a consumer, a healthcare provider, a state immunization registry, and so forth, one skilled in the art can appreciate that similar features and principles may be applied to other industries.

While the exemplary embodiments described herein are described in sufficient detail to enable those skilled in the art to practice principles of the present disclosure, it should be understood that other embodiments may be realized and that logical and/or functional changes may be made without departing from the spirit and scope of the present disclosure. Thus, the detailed description herein is presented for purposes of illustration and not of limitation.

While the description references specific technologies, system architectures and data management techniques, practitioners will appreciate that this description is of various embodiments, and that other devices and/or methods may be implemented without departing from the scope of principles of the present disclosure. Similarly, while the description references a user interfacing with the system via a computer user interface, practitioners will appreciate that other interfaces may include mobile devices, kiosks and handheld devices such as mobile phones, smart phones, tablet computing devices, etc.

While the steps outlined herein represent exemplary embodiments of principles of the present disclosure, practitioners will appreciate that there are any number of computing algorithms and user interfaces that may be applied to create similar results. The steps are presented for the sake of explanation only and are not intended to limit the scope of the present disclosure in any way. Benefits, other advantages, and solutions to problems have been described herein with regard to specific embodiments. However, the benefits, advantages, solutions to problems, and any element(s) that may cause any benefit, advantage, or solution to occur or become more pronounced are not to be construed as critical, required, or essential features or elements of any or all of the claims.

It should be understood that the detailed description and specific examples, indicating exemplary embodiments, are given for purposes of illustration only and not as limitations. Many changes and modifications may be made without departing from the spirit thereof, and principles of the present disclosure include all such modifications. Corresponding structures, materials, acts, and equivalents of all elements are intended to include any structure, material, or acts for performing the functions in combination with other elements. Reference to an element in the singular is not intended to mean "one and only one" unless explicitly so stated, but rather "one or more." Moreover, when a phrase similar to "at least one of A, B, or C" or "at least one of A, B, and C" is used in the claims or the specification, the phrase is intended to mean any of the following: (1) at least one of A; (2) at least one of B; (3) at least one of C; (4) at least one of A and at least one of B; (5) at least one of B and at least one of C; (6) at least one of A and at least one of C; or (7) at least one of A, at least one of B, and at least one of C.

What is claimed is:

1. A networked database system including one or more software applications for operation on a user device, the system comprising:

one or more processors configured for manipulation of health records associated with a user;

one or more tangible, non-transitory electronic memories in electronic communication with the one or more processors, the one or more tangible, non-transitory memories having instructions stored thereon that, in response to execution by the one or more processors, cause the one or more processors to perform operations comprising:

receiving, by the one or more processors, an authorization request to access the networked database system;

transmitting, by the one or more processors, a request for at least one of a health care provider, a lab provider, or a state immunization database to approve access of the user to the networked database system;

receiving, by the one or more processors, approval for access of the user to the networked database system;

transmitting, by the one or more processors and to an electronic immunization registry system of a first state, a Health Level 7 (HL7) formatted request for a first state electronic immunization records of the user;

receiving, by the one or more processors and from the electronic immunization registry system of the first state, the first state electronic immunization records of the user in an HL7 compatible format;

receiving, by the one or more processors and from a computer based system associated with at least one of the lab provider or a healthcare provider, electronic health records associated with the user;

integrating, by the one or more processors, the first state electronic immunization records of the user and the electronic health records associated with the user to form an integrated data comprising associated electronic health and immunization records of the user, wherein the integrating comprises:
designating, by the one or more processors, a key field in data tables;
performing, by the one or more processors and using the key field, a key field search that matches the first state electronic immunization records of the user and the electronic health records associated with the user to form the integrated data;
when the key field search does find a match for a respective record:
determining when the integrated data comprises an unmet requirement; and
initiating a scheduling process to fulfill the unmet requirement; and
when the key field search does not find a match for a respective record:
initiating, by the one or more processors, a record matching fault process; and
reporting, by the one or more processors, a discrepancy identified by the key field search to at least one of the health care provider, the lab provider, or the state immunization database for resolution.

2. The system of claim 1, further comprising a micro-application operative on the user device, the micro-application comprising an electronic database resident in the one or more tangible, non-transitory memories and a consumer software module accessible by the user of the user device, wherein the micro-application is operative to:
receive the integrated data from the one or more processors;
format the integrated data in a matrix barcode format; and
display on a display of the user device the matrix barcode formatted integrated data.

3. The system of claim 2, wherein the micro-application is further operative to:
receive from the user and via an input component of the user device the authorization request;
transmit over a network connection of the user device and to the computer based system associated with at least one of the health care provider, the lab provider, or the state immunization database the request to approve access of the user to the networked database system;
receive over the network connection of the user device and from the computer based system associated with at least one of the health care provider, the lab provider, or the state immunization database, approval for access of the user to the networked database system; and
display on the display of the user device, the integrated data.

4. The system of claim 1, wherein the integrating further comprises:
sorting, by the one or more processors, the integrated data of the user according to a known order to simplify a lookup process.

5. The system of claim 3, wherein the micro-application is configured to export, from the networked database system and responsive to a request from the user, at least a portion of the integrated data to an external records recipient.

6. The system of claim 5, wherein the at least the portion of the integrated data is exported in BlueButton+ format.

7. The system of claim 3, wherein the micro-application is configured to provide, to the user and within the networked database system, access to immunization information for a relative of the user.

8. The system of claim 3, wherein the micro-application is further operative to provide, to the electronic immunization registry system of the first state and responsive to a request from the user, electronic immunization records obtained from an electronic immunization registry system of a second state.

9. The system of claim 1, wherein the operations further comprise:
receiving, by the one or more processors, corrected first state electronic immunization records for the user;
updating, by the one or more processors, the integrated data of the user based on the corrected first state electronic immunization records; and
providing, by the one or more processors and to the electronic immunization registry system of the first state, the corrected first state electronic immunization records for the user.

10. The system of claim 8, wherein the micro-application is further operative to:
generate, for the user and based on the integrated data, an official state immunization form for the user for at least one of the first state or the second state.

11. The system of claim 3, wherein the micro-application is further operative to:
generate, for the user and based at least partially on the integrated data, a reminder regarding a suggested immunization for at least one of the user or a member of a household of the user; and
deliver, via the display of the user device and to the user, the reminder regarding the suggested immunization.

12. The system of claim 1, wherein the networked database system further comprises a provider module operative on a computer associated with the healthcare provider, the provider module operative to:
receive a request for the healthcare provider to approve access of the user to the networked database system;
receive, from the healthcare provider and via a web page, approval for access of the user to the networked database system; and
transmit, to the user device, approval for access of the user to the networked database system.

13. The system of claim 1, wherein the operations further comprise:

comparing, by the one or more processors, the integrated electronic immunization record for the user against a recommended immunization schedule provided by the United States Center for Disease Control; and displaying, by the one or more processors and via a display of the user device, a prompt displaying a recommended immunization for the user is approaching a due date or is past due.

14. The system of claim 1, wherein the receiving the first state electronic immunization records of the user and the receiving the second state electronic immunization records of the user are performed without the user being required to create a read-only account with at least one of the electronic immunization registry system of the first state or the electronic immunization registry system of the second state.

15. The system of claim 1, wherein the integrated data comprises at least one of a record of immunizations associated with a consumer health record, immunization-related information, and lab related information.

16. The system of claim 1, wherein the operations further comprise:

transmitting, by the one or more processors, the integrated data for the user to at least one of a third party system or the user device.

17. A networked database system comprising:

one or more processors configured for manipulation of user immunization records;

one or more tangible, non-transitory electronic memories in electronic communication with the one or more processors; and a micro-application operative on a mobile device, the micro-application comprising an electronic database resident in the one or more tangible, non-transitory electronic memories and a consumer software module accessible by a user of a user device, wherein the micro-application:

receives, from the user and via an input component of the user device, an authorization request for the user to access the networked database system;

transmits, over a network connection of the user device and to an electronic immunization registry system of a first state, a Health Level 7 (HL7) formatted request for a first state electronic immunization records of the user;

receives, over the network connection of the user device and from the electronic immunization registry system of the first state, the first state electronic immunization records of the user in an HL7 compatible format;

transmits, over the network connection of the user device and to an electronic immunization registry system of a second state, a Health Level 7 (HL7) formatted request for second state electronic immunization records of the user;

receives, over the network connection of the user device and from the electronic immunization registry system of the second state, the second state electronic immunization records of the user in the HL7 compatible format;

integrates, in the electronic database of the micro-application, the first state electronic immunization records of the user and the second state electronic immunization records of the user to form an integrated electronic immunization record of the user, wherein the integrating comprises:

designating, by the one or more processors, a key field in data tables;

performing, by the one or more processors and using the key field, a key field search that matches the first state electronic immunization records of the user and the electronic health records associated with the user to form the integrated electronic immunization record of the user;

when the key field search does find a match for a respective record:

determining when the integrated electronic immunization record of the user comprises an unmet requirement; and initiating a scheduling process to fulfill the unmet requirement; and when the key field search does not find a match for a respective record:

initiating, by the one or more processors, a record matching fault process; and reporting, by the one or more processors, a discrepancy identified by the key field search to at least one of a health care provider, a lab provider, or a state immunization database for resolution; and displays, on a display of the mobile device, the integrated electronic immunization record for the user.

18. The networked database system of claim 17, wherein the micro-application:

transmits, over the network connection of the user device and to a computer associated with the health care provider, a request for the health care provider to approve access of the user to the networked database system; and receives, over the network connection of the user device and from the computer associated with the health care provider, approval for access of the user to the networked database system.

19. A method comprising:

providing a networked database system comprising:

one or more processors configured for manipulation of user immunization records;

one or more tangible, non-transitory electronic memories in electronic communication with the one or more processors; and a software application operative on the one or more processors, the software application comprising a consumer software module accessible to a user of the networked database system;

authenticating the user to access the networked database system via the consumer software module;

transmitting, over a network connection of the networked database system and to an electronic immunization registry system of a first state, a Health Level 7 (HL7) formatted request for a first state electronic immunization records of the user;

receiving, over the network connection of the networked database system and from the electronic immunization registry system of the first state, the first state electronic immunization records of the user in an HL7 compatible format;

transmitting, over the network connection of the networked database system and to an electronic immunization registry system of a second state, a Health Level 7 (HL7) formatted request for second state electronic immunization records of the user;

receiving, over the network connection of the networked database system and from the electronic immunization registry system of the second state, the second state electronic immunization records of the user in the HL7 compatible format;

integrating, in an electronic database, the first state electronic immunization records of the user and the second state electronic immunization records of the user to form an integrated electronic immunization record of the user, wherein the integrating comprises:

designating, by the one or more processors, a key field in data tables;

performing, by the one or more processors and using the key field, a key field search that matches the first state electronic immunization records of the user and the electronic health records associated with the user to form the integrated electronic immunization record of the user;

when the key field search does find a match for a respective record:

determining when the integrated electronic immunization record of the user comprises an unmet requirement; and initiating a scheduling process to fulfill the unmet requirement; and when the key field search does not find a match for a respective record;

initiating, by the processor one or more processors, a record matching fault process; and reporting, by the one or more processors, a discrepancy identified by the key field search to at least one of a health care provider, a lab provider, or a state immunization database for resolution; and providing, to the user, the integrated electronic immunization record for the user.

20. The method of claim 19, wherein the consumer software module is accessible to the user via a webpage and wherein the integrated electronic immunization record is provided to the user via the webpage.

21. The method of claim 19, wherein the software application comprises an electronic database resident in the one or more tangible, non-transitory electronic memories.

* * * * *